US008617897B2

(12) United States Patent
Menon

(10) Patent No.: US 8,617,897 B2
(45) Date of Patent: Dec. 31, 2013

(54) METHOD OF DETECTING OXIDES OF NITROGEN

(75) Inventor: Vinod P. Menon, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 13/388,564

(22) PCT Filed: Aug. 3, 2010

(86) PCT No.: PCT/US2010/044240
§ 371 (c)(1),
(2), (4) Date: Feb. 2, 2012

(87) PCT Pub. No.: WO2011/017317
PCT Pub. Date: Feb. 10, 2011

(65) Prior Publication Data
US 2012/0129266 A1 May 24, 2012

Related U.S. Application Data

(60) Provisional application No. 61/231,257, filed on Aug. 4, 2009, provisional application No. 61/369,933, filed on Aug. 2, 2010.

(51) Int. Cl.
G01N 33/48 (2006.01)
G01N 21/78 (2006.01)

(52) U.S. Cl.
USPC ............. 436/116; 436/63; 436/106; 436/110; 436/118; 436/164; 436/166; 436/174; 436/178; 422/527; 422/535

(58) Field of Classification Search
USPC ........... 436/63, 106, 110, 116, 118, 164, 166, 436/174, 177, 178; 422/430, 68.1, 527, 422/534, 535
See application file for complete search history.

(56) References Cited

U.S. PATENT DOCUMENTS

| | | | | |
|---|---|---|---|---|
| 3,817,705 A | * | 6/1974 | Stein et al. | 436/110 |
| 4,003,706 A | | 1/1977 | Szekely | |
| 4,434,235 A | | 2/1984 | Rabi et al. | |
| 4,631,255 A | * | 12/1986 | Takino et al. | 435/37 |
| 6,573,108 B1 | * | 6/2003 | Hardman et al. | 436/518 |
| 2007/0048182 A1 | | 3/2007 | Song et al. | |
| 2008/0274551 A1 | | 11/2008 | Chinchilla | |

FOREIGN PATENT DOCUMENTS

| | | |
|---|---|---|
| GB | 1 282 653 | 7/1972 |
| GB | 2 442 748 | 4/2008 |
| WO | WO 2006/079167 | 8/2006 |
| WO | WO 2008/119974 | 10/2008 |
| WO | WO 2011/017325 | 2/2011 |

OTHER PUBLICATIONS

Bryan, N. S. et al.; "Methods to detect nitric oxide and its metabolites in biological samples"; Free Radical Biology & Medicine; vol. 43; 2007;pp. 645-657.

(Continued)

Primary Examiner — Maureen Wallenhorst

(57) ABSTRACT

Methods and kits to detect and quantitate $NO_x$ compounds in a biological sample are provided. The methods include reacting a mixture that includes a nitrite compound and a chromogenic reagent to form a colored compound, contacting the mixture with a retention medium configured to retain the colored compound, and detecting the colored compound retained on the retention medium.

11 Claims, 5 Drawing Sheets

(56) References Cited

OTHER PUBLICATIONS

Capitán-Vallvey, L.F. et al.; "Test strip for determination of nitrite in water", Anal. Bioanal. Chem., vol. 373, 2002; pp. 289-294. (XP-002602789).

Fanning, J.C., "The chemical reduction of nitrate in aqueous solution", Coordination Chemistry Reviews, vol. 199; 2000, pp. 159-179.

Gu, X. et al.; "Determination of trace nitrite ion in water by spectrophotometric method after preconcentration on an organic solvent-soluble membrane filter", Talanta; vol. 43, 1996; pp. 169-175, (XP-002602788).

Miranda, K.M. et al., "A Rapid, Simple Spectrophotometric Method for Simultaneous Detection of Nitrate and Nitrite", Nitric Oxide: Biology and Chemistry, vol. 5, No. 1; 2001; pp. 62-71.

Sawicki, E. et al.; "Comparison of fifty-two spectrophotometric methods for the determination of nitrite", Talanta, vol. 10, 1963; pp. 641-655.

Sonoda, M. et al.; "An Assay Method for Nitric Oxide-Related Compounds in Whole Blood", Analytical Biochemistry, vol. 247, 1997; pp. 417-427.

* cited by examiner

METHOD OF DETECTING OXIDES OF NITROGEN

CROSS REFERENCE TO RELATED APPLICATIONS

This application claims priority to U.S. Provisional Patent Application Nos. 61/231,257, filed Aug. 4, 2009 and 61/369,933, filed Aug. 2, 2010, which are incorporated herein by reference.

BACKGROUND

Nitrate compounds can be found in water supplies and, at elevated levels, can cause gastric problems related to nitrosamine in adults and can cause methemoglobinemia in infants. Drinking water standards typically include maximum allowable concentrations of nitrate compounds in public drinking water.

Nitrate compounds can also be found in low levels in biological tissue and, in particular, wound tissue. Nitric oxide synthase (NOS) produces nitric oxide (NO) in the tissue. The NO has a half-life of about 5 seconds in biological tissues. NO is normally metabolized to stable NO-related compounds (e.g., nitrate and nitrite compounds), which may be assayed in urine, plasma, tissue, wound fluid, or other specimens from a patient. The level of nitrate or nitrite compounds in a specimen can serve as an indicator of the level of NO synthesis in a patient. Below a threshold level of NO in a patient, normal wound repair is not achieved, resulting in a chronically non-healing wound or ulceration.

There is a need for simple, sensitive methods for measuring NO-related compounds in a sample.

SUMMARY

The present disclosure relates to methods for the detection and, optionally, quantitation of $NO_x$ compounds in a biological sample (e.g., urine, plasma, tissue, wound fluid, or other specimens from a patient). In certain preferred embodiments, the biological sample is obtained from a site may comprise a limited amount of instantaneously capturable fluid (e.g., a wound site). The biological sample may be captured by a sample acquisition device. The inventive methods provide for the detection of extremely low quantities of $NO_x$ compounds in a biological sample.

In one aspect, the present disclosure provides a method of detecting $NO_x$ compounds. The method can comprise providing a sample suspected of containing a $NO_x$ compound, and 4,4'-sulfonyldianiline; forming a mixture comprising the sample and the 4,4'-sulfonyldianiline; and detecting a colored precipitate that indicates the presence of $NO_x$ in the sample. The mixture can further comprise N-(1-naphthyl)ethylene-diamine and/or $VCl_3$.

In another aspect, the present disclosure provides a method of detecting $NO_x$ compounds in a wound. The method can comprise a sample from a wound, and 4,4'-sulfonyldianiline; forming a mixture comprising the sample and the 4,4'-sulfonyldianiline; and detecting a colored precipitate that indicates the presence of $NO_x$ in the sample. The mixture can further comprise N-(1-naphthyl)ethylene-diamine, and/or $VCl_3$.

In another aspect, the present disclosure provides a method of detecting $NO_x$ compounds. The method can comprise providing a sample suspected of containing a $NO_x$ compound, 4,4'-sulfonyldianiline, and an aromatic diamine; forming a mixture comprising the sample, the 4,4'-sulfonyldianiline, and the aromatic diamine; and detecting a colored precipitate that indicates the presence of $NO_x$ in the sample. The aromatic diamine can comprise N-(1-naphthyl)ethylene-diamine.

In another aspect, the present disclosure provides a method of detecting $NO_x$ compounds in a wound. The method can comprise providing a sample acquisition device, a sample from a wound, 4,4'-sulfonyldianiline, and an aromatic diamine; forming a mixture comprising the sample and the 4,4'-sulfonyldianiline, and the aromatic diamine; and detecting a colored compound that indicates the presence of $NO_x$ in the sample. The aromatic diamine can comprise N-(1-naphthyl)ethylene-diamine.

In any of the above embodiments, the mixture further can comprise a strong acid. In any of the above embodiments, the colored precipitate can comprise a red-colored precipitate.

In any of the above embodiments, the method further can comprise the step of heating the mixture. In any of the above embodiments, the method further can comprise the step of filtering at least a portion of the mixture. In some embodiments, filtering at least a portion of the mixture can comprise capturing a filtrate in a filter-type retention medium with a surface area of about 1.5 $mm^2$ to about 31 $mm^2$. In some embodiments, filtering at least a portion of the mixture can comprise capturing a filtrate in a filter-type retention medium with a surface area of about 1.5 $mm^2$ to about 20 $mm^2$. In some embodiments, filtering at least a portion of the mixture can comprise capturing a filtrate in a filter-type retention medium with a surface area of about 1.5 $mm^2$ to about 3.1 $mm^2$.

In any of the above embodiments, detecting the colored precipitate can comprise detecting the precipitate visually. In any of the above embodiments, detecting a colored precipitate can comprise detecting the colored precipitate quantitatively.

In any of the above embodiments, the method further can comprise forming a mixture comprising a predetermined amount of a $NO_x$ compound and 4,4'-sulfonyldianiline. In these embodiments, the method further can comprise detecting a colored precipitate. In these embodiments, the method further can comprise comparing the amount of colored precipitate in the mixture comprising the sample suspected of containing a $NO_x$ compound with the amount of colored precipitate in the sample comprising a predetermined amount of a $NO_x$ compound.

In another aspect, the present disclosure provides a kit. The kit can comprise a filter-type retention medium and a compound selected from the group consisting of 4,4'-sulfonyldianiline and N-(1-naphthyl)ethylene-diamine.

In another aspect, the present disclosure provides a kit. The kit can comprise a filter-type retention medium and two or more compounds selected from the group consisting of 4,4'-sulfonyldianiline, N-(1-naphthyl)ethylene-diamine, and $VCl_3$.

In any of the above embodiments, the kit can further comprise a strong acid. In any of the above embodiments, the kit can further comprise a sample acquisition device. In some embodiments, the sample acquisition device can be adapted for obtaining a sample from a wound. In any of the above embodiments, the kit can further comprise a filtration device.

In one aspect, the present disclosure provides a method of detecting a $NO_x$ compound in a wound. The method can comprise providing a sample from a wound, and a chromogenic that reacts with a nitrite compound to form a colored compound. The method further can comprise forming a first mixture comprising the sample and the chromogenic. The method further can comprise contacting at least a portion of the first mixture with a first retention medium configured to retain the colored compound. The method further can comprise detecting the colored compound retained on the first retention medium.

In some embodiments, the method further can comprise providing a reducing agent capable of reducing a nitrate compound to a nitrite compound, wherein the first mixture includes the reducing agent.

In any of the above embodiments of the method, the chromogenic that reacts with a nitrite compound to form a colored compound can comprise a chromogen or a developing agent. In any of the above embodiments of the method, the chromogenic that reacts with a nitrite compound to form a colored compound can be selected from the group consisting of, 4,4'-Bis-(dimethylamino)thiobenzophenone; azulene; brucine indol; p-phenylazoaniline; p-nitroaniline; anthranilic acid; p-aminoacetophenone; p-aminophenylsulphone; p-phenylaniline; sulphanilic acid; bis-(4-aminophenyl)sulphide; (4-aminophenyl)trimethylammonium chloride; 1-naphthylamine; chloro-p-phenylenediamine; resorcinol; N,N-dimethylaniline; p-aminoacetophenone; 4-nitro-1-naphthylamine; p-nitroaniline; 4-nitro-1-naphthylamine; p-phenylazoaniline; p-phenylazoaniline; p-nitroaniline; 4-nitro-1-naphthylamine; p-aminoacetophenone; 1-naphthylamine; 1-anilinonaphthylene; 1-naphthol; benzaldehyde 2-benzothiazolylhydrazone; anthrone; 1-anthrol; azulene; diphenylamine; 1,2-dihydroxybenzene; sesamol; N,N-dimethyl-1-naphthylamine; formaldehyde; iron(III) perchlorate; and N,N-dimethyl-3-hydroxy aniline.

In any of the above embodiments, the method further can comprise the step of heating the mixture. In any of the above embodiments of the method, contacting at least a portion of the mixture with a first retention medium can comprise contacting the portion with a membrane filter. In any of the above embodiments of the method, detecting a colored compound can comprise detecting the colored compound quantitatively.

In any of the above embodiments, the method further can comprise providing a second retention medium, a chromogenic, and a solution comprising a predetermined amount of a $NO_x$ compound. The chromogenic reacts with a nitrite compound to form a colored compound. The second retention medium is configured to retain the colored compound. The method further can comprise forming a second mixture including the solution and the chromogenic, contacting at least a portion of the second mixture with a second retention medium, detecting the colored compound retained on the second retention medium, and comparing the amount of colored compound retained on the first retention medium with the amount of colored compound retained on the second retention medium.

In another aspect, the present disclosure provides a kit. The kit can comprise a retention medium configured to retain a colored compound and a chromogenic that reacts with a nitrite compound to form the colored compound.

In some embodiments, the kit further can comprise an agent to reduce a nitrate compound to a nitrite compound. In any of the above embodiments, the kit further can comprise a sample acquisition device. In any of the above embodiments, the kit can further comprise a filtration device that includes the retention medium.

DEFINITIONS

"$NO_x$", as used herein, refers to nitric oxide-related (NO-related) compounds. NO-related compounds include nitric oxide and derivatives thereof. NO derivatives include nitrate compounds and nitrite compounds.

The use of "including," "comprising," or "having" and variations thereof herein is meant to encompass the items listed thereafter and equivalents thereof as well as additional items. Unless specified or limited otherwise, the term "coupled", "attached", "connected" and variations thereof is used broadly and encompasses both direct and indirect couplings. Further, the term "coupled" is not restricted to physical or mechanical couplings. It is to be understood that other embodiments may be utilized, and structural or logical changes may be made without departing from the scope of the present disclosure. Furthermore, terms such as "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, "a," "an," "the," "at least one," and "one or more" are used interchangeably. Thus, for example, an article that comprises "a" sample-collecting region can be interpreted to mean that the article includes "one or more" sample-collecting regions. Similarly, a method for detecting "an" analyte can be interpreted to mean that the method can involve detecting "one or more" analyte.

The term "and/or" means one or all of the listed elements or a combination of any two or more of the listed elements.

As used herein, the term "or" is generally employed in its sense including "and/or" unless the content clearly dictates otherwise.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE DRAWINGS

The present invention will be further explained with reference to the drawing figures listed below, where like structure is referenced by like numerals throughout the several views.

DETAILED DESCRIPTION

Figure 1A:
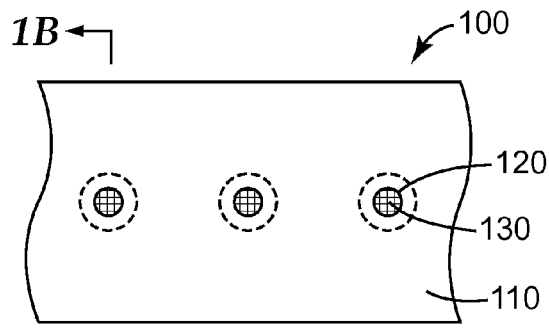
FIG. 1A is a top view of one embodiment of a device for detecting a nitrate compound or a nitrite compound according to the present disclosure.

The present disclosure generally relates to articles and methods for detecting oxides of nitrogen (e.g., nitrite and/or nitrate compounds) in a sample. The present disclosure further relates to articles and methods to assess the status of a wound. The inventive articles and methods provide a rapid test to measure relatively low (e.g., physiological) levels of $NO_x$ in a sample.

In some embodiments, the inventive methods include collecting a soluble colored compound or a colored precipitate, which is indicative of a nitrite compound or a nitrate compound, in a filter. In some embodiments, the precipitate can be collected in a filter with a relatively small cross-sectional area. Advantageously, collection of the precipitate in a filter with a relatively small cross-sectional area can permit the detection or quantitation of very low levels of $NO_x$ compounds in a sample.

Samples and Sample Collection:

Methods of the present disclosure can be used to detect $NO_x$ compounds in a variety of samples including, but not limited to, water (e.g., surface water, pond water, well water, process water, potable water), agriculture samples (e.g., waste lagoons, livestock feed, crops, soil), food products (e.g., vegetables, dairy products), and patient samples (e.g., blood, urine, tissue, plasma, wounds, wound exudate).

Methods of the present disclosure can be used in conjunction with a variety of sample acquisition devices. Preferred sample acquisition devices (e.g., pipets, swabs, sponges, wound dressings, and the like) are substantially free of reactive nitrite or nitrate compounds. Examples of suitable sample acquisition devices are described in U.S. Patent Application No. 61/231,236, filed Aug. 4, 2009, and entitled, "SAMPLING DEVICES AND METHODS OF USE", which is incorporated herein by reference in its entirety.

The sample acquisition device may be adapted for obtaining a sample from a wound. For example, in some embodiments, adapting the sample acquisition device for obtaining a sample from a wound may comprise processing the device to substantially decontaminate, disinfect, or to sterilize the device. In some embodiments, adapting the sample acquisition device for obtaining a sample from a wound may comprise packaging the sample acquisition device in a package that has been processed to substantially decontaminate, disinfect, or sterilize the package. In some embodiments, adapting the sample acquisition device for obtaining a sample from a wound may comprise constructing the sample acquisition device from materials that readily absorb or adsorb wound exudate. In some embodiments, adapting the sample acquisition device for obtaining a sample from a wound may comprise providing an absorbent material with a wound-facing layer selected to resist adhesion to wound tissue.

Devices for collecting a sample releasably acquire (e.g., by adsorption and/or absorption) an amount of sample (e.g., wound exudate) sufficient to perform one or more test procedures.

Method of Detecting a Nitrate or Nitrite Compound in a Sample:

Methods of the present disclosure include detecting a $NO_x$ compound in a sample. Methods of the present disclosure further include detecting $NO_x$ in a wound exudate sample. NO is normally metabolized to certain stable products such as nitrate and nitrite compounds, which may be assayed in urine, plasma, tissue, wound fluid, or other specimens from a patient. The level of nitrate compounds, nitrite compounds, or other NO-related products in a specimen serves as an indicator of the level of NO synthesis in a patient.

The "level" of NO-related product or oxidant stress-related product usually refers to the concentration (in moles per liter, micromoles per liter, or other suitable units) of the respective product in the specimen, or in the fluid portion of the specimen. However, other units of measure can also be used to express the level of the products. For example, an absolute amount (in micrograms, milligrams, nanomoles, micromoles, moles, or other suitable units) can be used, particularly if the amount refers back to a constant amount, mass, or volume of patient specimen (e.g., grams, kilograms, milliliters, liters, or other suitable units).

In one aspect, the present disclosure provides a method for detecting $NO_x$ compounds in a sample using a reaction that forms a colored compound (e.g., a red cationic dye that is similar or identical to Compound I, shown below):

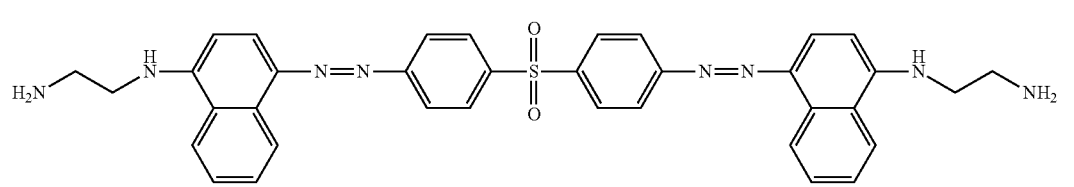

Compound I

In some embodiments, the method comprises providing a sample, a retention medium, and a chromogenic. The chromogenic is capable of reacting with a nitrite compound to form a colored compound. The retention medium is configured to retain the colored compound. The method further comprises forming a mixture comprising the sample and the chromogenic under conditions that permit the reaction of a nitrite compound with the chromogenic to form the colored compound, contacting at least a portion of the mixture with the retention medium, and detecting the colored compound retained on the retention medium.

The sample can be any sample that is suspected of containing nitrate compounds and/or nitrite compounds. The method is particularly suitable for use with relatively small-volume samples (e.g., about 2 µl to about 10 µl) containing relatively low cumulative concentrations (e.g., ≤50 µM) of nitrate and/or nitrite compounds. The sample may be a biological sample (e.g., urine, plasma, tissue, wound fluid, or other specimens from a patient). Embodiments of the method are particularly suitable for use with sample of wound fluid because i) it can be difficult instantaneously to obtain more than 10 microliters of wound fluid from a wound site and ii) samples of biological materials typically have relatively low concentrations (e.g., ≤50 µM, ≤40 µM, ≤30 µM, ≤20 µM, or ≤10 µM) of $NO_3$ and/or $NO_2$ compounds present in the sample material.

The retention medium can be any medium that is configured to capture and retain the colored compound. The colored compound may be captured and retained, for example, by absorption, adsorption, and/or filtration. Adsorption may be facilitated by hydrophobic and/or coulombic (ionic) interaction. Filtration may include the capture of the colored compound on the surface of and/or within the pores of a filter. In some embodiments, retention media exhibit anisotropic capture and retention of the colored compound (e.g., they capture and retain the colored compound at or near a surface of the media). Examples of suitable retention media include sheet media (i.e., substantially planar sheets of material such as, for example, plastic films, membrane filters, and nonwoven materials) and particles. In some embodiments, the particles may be porous particles. In some embodiments, the particles may be embedded in a matrix (e.g., fibers, microfibers, or a hydrogel) that does not substantially capture or retain the colored compound. The retention medium may comprise ionic groups that interact with ionic groups in the colored compound, thereby capturing and retaining the colored compound on and/or in the retention medium. Nonlimiting examples of suitable ionic groups for capturing and retaining a cationic colored compound include sulfonate, carboxylate, phosphate, sulfate ester, and phosphate ester groups. Nonlimiting examples of suitable ionic groups for capturing and retaining anionic colored compounds include a variety of quaternary amine, phosphonium, and sulfonium groups.

The method includes the use of a chromogenic reagent capable of reacting with a nitrite compound to form a colored compound. The chromogenic reagent can comprise at least one of a variety of chromogenic reagents known in the art, including chromogenic reagents described in a publication by E. Sawicki, et al. (1963) entitled "Comparison of fifty-two spectrophotometric methods for the determination of nitrite" (Talanta, vol. 10, pp. 641-655; Pergamon Press Ltd., Oxford, UK), which is incorporated herein by reference in its entirety. Chromogenic reagents include chromogens and developing agents. Chromogens can react with a developing agent to form anionic colored compounds. Suitable chromogens to form cationic colored compounds include, for example, diarylmethane cations (e.g., 4,4'-Bis-(dimethylamino)thiobenzophenone), diarylamine cations (e.g., azulene, brucine indol), bisazo dye dications (e.g., p-phenylazoaniline), azo dye cations (e.g., p-nitroaniline, anthranilic acid, p-aminoacetophenone, p-aminophenylsulphone, p-phenylaniline, sulphanilic acid, bis-(4-aminophenyl)sulphide, (4-aminophenyl)trimethylammonium chloride, and 1-naphthylamine), diazonium cations (e.g., chloro-p-phenylenediamine), and phenoxazine dications (e.g., resorcinol; N,N-dimethylaniline). Suitable chromogens to form anionic colored compounds include, for example, azo dye anions (e.g., p-aminoacetophenone, 4-nitro-1-naphthylamine, p-nitroaniline, 4-nitro-1-naphthylamine), triazene anions (e.g., p-phenylazoaniline), and formazan anions (e.g., p-phenylazoaniline, p-nitroaniline, 4-nitro-1-naphthylamine, p-aminoacetophenone)

Developing agents include a variety of developing agents known in the art. Typically, a particular developing agent is used in conjunction with a particular chromogen to yield a specific colored compound when the chromogen and the developing agent are reacted with $NO_2^-$ (see Sawicki et al., 1963). Suitable developing agents include, for example, 1-naphthylamine; 1-anilinonaphthylene; 1-naphthol; benzaldehyde 2-benzothiazolylhydrazone; anthrone; 1-anthrol; azulene; diphenylamine; 1,2-dihydroxybenzene; sesamol; N,N-dimethyl-1-naphthylamine; formaldehyde; iron(III) perchlorate; and N,N-dimethyl-3-hydroxyaniline).

In some embodiments, the method comprises forming a mixture comprising a sample suspected of containing a $NO_x$ compound, a chromogenic reagent (e.g., 4,4'-sulfonyldianiline), a developing agent (e.g., an aromatic diamine such as N-(1-naphthyl)-ethylenediamine), and an acid (e.g., HCl). The method further comprises detecting a colored compound (e.g., soluble compound or a precipitate) that indicates the presence of $NO_x$ in the sample.

The mixture is formed under conditions that permit the reaction of a nitrite compound with the chromogenic reagent to form a colored compound. Suitable conditions are known and are described, for example, by E. Sawicki, et al. As shown in Reaction Scheme I, the conditions include an acid (e.g., HCl, $H_3PO_4$, $H_2SO_4$, acetic acid, formic acid) to facilitate the formation of the colored compound. In some embodiments, the conditions may include an elevated temperature (e.g., about 70° C.) to increase the rate of formation of the colored compound.

In some embodiments of the method, the mixture further can comprise a reducing agent (e.g., $VCl_3$) that can drive the reduction of a nitrate compound to a nitrite compound. In the embodiments wherein $VCl_3$ is used as the reducing agent, HCl is the preferred acid i) to stabilize the $VCl_3$ and ii) to facilitate the formation of the colored compound. Other suitable reducing agents include, for example, active metals (e.g., Cd, Al, Zn), ammonia, and borohydride. In certain alternative embodiments, the mixture can be subjected to a process (e.g., electrochemical reduction, photochemical reduction) that drives the reduction of a nitrate compound to a nitrite compound. Methods for reducing a nitrate compound to a nitrite compound are described in a paper by J. C. Fanning ("The chemical reduction of nitrate in aqueous solution"; Coordination Chemistry Reviews, volume 199, pages 159-179; 2000; Elsevier, New York, N.Y.), which is incorporated herein by reference in its entirety.

In one embodiment, the method comprises forming a mixture comprising a sample suspected of containing a $NO_x$ compound and 4,4'-sulfonyldianiline. The method further comprises detecting a colored precipitate that indicates the presence of $NO_x$ in the sample. In some embodiments, the mixture further can comprise N-(1-naphthyl)-ethylenediamine. In some embodiments, the mixture further can comprise $VCl_3$. In some embodiments, the mixture further can comprise a strong acid (e.g., HCl).

In one embodiment, the method comprises forming a mixture comprising a sample suspected of containing a $NO_x$ compound, 4,4'-sulfonyldianiline, and an aromatic diamine. The method further comprises detecting a colored compound that indicates the presence of $NO_x$ in the sample. In some embodiments, the aromatic diamine comprises N-(1-naphthyl)-ethylenediamine. In some embodiments, the mixture further can comprise $VCl_3$. In some embodiments, the mixture further can comprise a strong acid (e.g., HCl).

In one embodiment, the method of detecting $NO_x$ compounds comprises forming a mixture including a sample suspected of containing a $NO_x$ compound, $VCl_3$, and 4,4'-sulfonyldianiline. The method further comprises detecting a colored compound that indicates the presence of $NO_x$ in the sample.

In one embodiment, the method of detecting a $NO_x$ compound comprises forming a mixture including a sample suspected of containing a $NO_x$ compound, N-(1-naphthyl)-ethylenediamine, and 4,4'-sulfonyldianiline. The method further comprises detecting a colored compound that indicates the presence of $NO_x$ in the sample.

In one embodiment, the method of detecting $NO_x$ compounds comprises forming a mixture including a sample suspected of containing a $NO_x$ compound, $VCl_3$, and N-(1-naphthyl)-ethylenediamine. The method further comprises detecting a colored compound that indicates the presence of $NO_x$ in the sample.

Without being bound by theory, Reaction Scheme I shows an exemplary proposed pathway for the formation of a colored dye to detect $NO_3^-$ (or $NO_2^-$) in a mixture comprising a nitrate (or a nitrite) compound, $VCl_3$, HCl, p-diaminodiphenyl sulfone (4,4'-sulfonyldianiline), and N-(1-naphthyl)-ethylenediamine:

Reaction Scheme I:

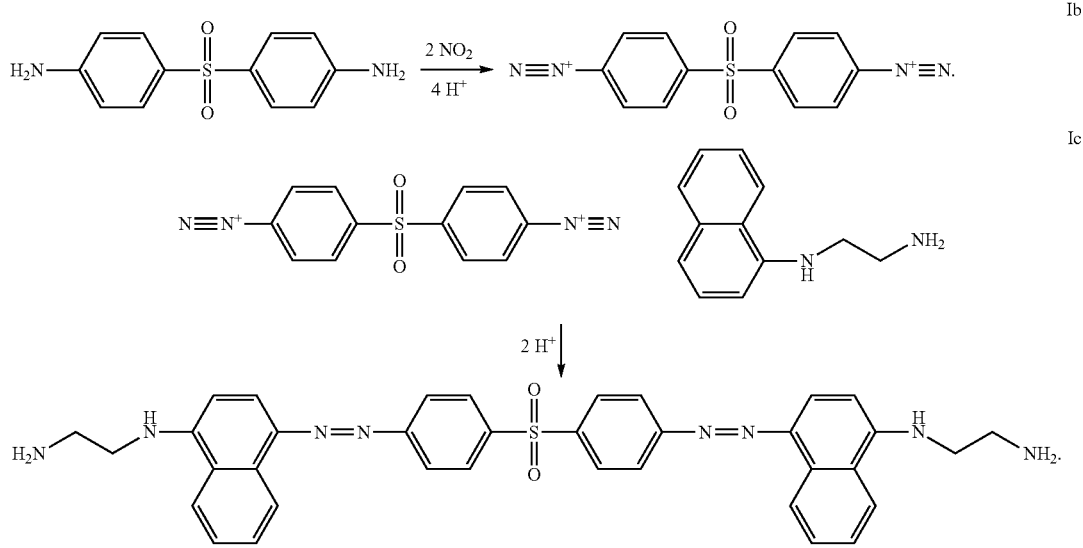

The proposed pathway can include the reduction of $NO_3^-$ to $NO_2^-$ in the presence of $VCl_2$ and a strong acid (HCl), as shown in reaction Ia. The proposed pathway further can include the oxidation of p-diaminodiphenyl sulfone in the presence of $NO_2^-$ and acid, as shown in reaction Ib. The proposed pathway further can include the coupling of two molecules of N-(1-naphthyl)-ethylenediamine to the oxidized form of p-diaminodiphenyl sulfone to form the colored reaction product, as shown in reaction Ic.

Forming a mixture comprising a sample suspected of containing a $NO_x$ compound, $VCl_3$, HCl, p-diaminodiphenyl sulfone, and/or N-(1-naphthyl)-ethylenediamine, in any combination of components, can comprise reacting the mixture at an elevated temperature. Elevated temperatures can be used to increase the rate of the reaction, provided the elevated temperature does not substantially decrease the accuracy, sensitivity, and/or reproducibility of the reaction. For example, a sample suspected of containing a $NO_x$ compound can be reacted with a mixture comprising $VCl_3$, HCl, p-diaminodiphenyl sulfone, and/or N-(1-naphthyl)-ethylenediamine at a temperature of about 70° C. A person of ordinary skill in the relevant art can easily determine whether the elevated temperature substantially decreases the accuracy, sensitivity, or reproducibility of the reaction by testing samples containing known amounts of $NO_x$ compound at ambient temperature and at an elevated temperature and comparing the measurements at both temperatures.

In one embodiment, a sample suspected of containing a $NO_x$ compound can be reacted in a mixture comprising $VCl_3$, HCl, p-diaminodiphenyl sulfone, and/or N-(1-naphthyl)-ethylenediamine, in any combination of components, for a period of time sufficient to form a detectable amount of a colored compound. In some embodiments, the colored compound comprises a red compound. In some embodiments, the colored compound comprises a precipitable colored compound. In a preferred embodiment, a sample suspected of containing a $NO_x$ compound can be reacted in a mixture comprising $VCl_3$, HCl, p-diaminodiphenyl sulfone, and N-(1-naphthyl)-ethylenediamine at 70° C. for about 10 minutes. The reaction can form a soluble or a precipitable, colored compound. The method further comprises contacting the mixture with a retention medium configured to retain the colored compound. In this embodiment, the method can be used to visually detect at least about 50 pmoles of a nitrite or nitrate compound, or combinations thereof, in a 10 microliter sample.

In any of the above embodiments, the method can further comprise cooling the reaction mixture. The reaction mixture can be cooled to room temperature, for example. In any of the above embodiments, the method can further comprise diluting the reaction mixture. The reaction mixture can be diluted with water (e.g., deionized water), for example. In some embodiments, a reaction mixture of about 170 microliters can be diluted with about 830 microliters of deionized water.

In some embodiments, the method further can comprise filtering all or at least a portion of the mixture or diluted mixture through a retention medium comprising a filter. The mixture can be filtered through any filtration media (e.g., a surface filter or a depth filter) that is suitable to retain the colored compound that is a product of the reaction. Non-limiting examples of suitable filtration-type retention media include polysulfone, cellulosic, glass membrane filters, and carboxylated nylon filters. Preferably, the filtration-type retention medium does not substantially interfere (e.g., obscure, dilute, or diffuse) with the visualization, detection, or quantitation of the colored compound. As used herein, collecting a soluble colored compound or colored precipitate "in" a retention medium (e.g., a filter medium) refers to collecting the precipitate on the surface of a retention medium (e.g., the surface of a membrane filter), in a filter-type retention medium (e.g., inside a depth filter), or both. Collecting the colored precipitate in a filter also refers to collecting the precipitate on a filter disposed in a compartment of a device, such as a 96-well filter plate, for example.

In some embodiments, filtering at least a portion of the mixture can comprise capturing a filtrate in a filter-type retention medium with a surface area greater than 31 mm$^2$. In some embodiments, filtering at least a portion of the mixture can comprise capturing a filtrate in a filter-type retention medium with a surface area of about 1.5 mm$^2$ to about 31 mm$^2$. In some embodiments, filtering at least a portion of the mixture can comprise capturing a filtrate in a filter-type retention medium with a surface area of about 1.5 mm$^2$ to about 20 mm$^2$. In some embodiments, filtering at least a portion of the mixture can comprise capturing a filtrate in a filter-type retention medium with a surface area of about 1.5 mm$^2$ to about 3.1 mm$^2$.

In some embodiments, the mixture is filtered through a membrane filter (I.C.E. 450, polysulfone membrane, 0.45 µm, part number 66530) available from Pall Gelman (East Hills, N.Y.). In some embodiments, the mixture is filtered through a membrane with a diameter of about 2 mm.

The filter-type retention medium may be disposed in a device (e.g., a filtration device) for filtering a liquid sample. The filtration device may comprise a mixing compartment, which can be used to form mixtures of compounds and samples according to the methods described herein. In some embodiments, the mixing compartment is in fluid communication with the filter-type retention medium or other retention media. In some embodiments, the mixing compartment is in selective fluid communication (e.g., via a valve) with the filter-type retention medium or other retention media.

The mixture containing the sample can be passed through a filter actively (e.g., by positive pressure applied to the sample or by negative pressure applied to the device comprising the filter) or the sample can be passed through the filter passively (e.g, by gravity flow or by applying a wicking composition to the side of the filter opposite the side that is in contact with the sample.

FIG. 1A shows a top view of one embodiment of a device 100 for detecting NO$_x$ compounds in a sample. The device comprises an upper layer 110 with a plurality of through-holes 120. The upper layer 110 is preferably constructed from a water-resistant material (e.g., plastic, metal, glass, coated paper). In some embodiments, the upper layer 110 is constructed from a plastic film (e.g., a vinyl tape). In some embodiments, the upper layer 110 may be formed (e.g., by injection molding) with through-holes 120. In some embodiments, the through-holes 120 can be formed (e.g., via a hole punch or perforator) after the upper layer 110 is formed. Positioned beneath the upper layer 110 and coextensive with the cross-sectional area of the through-holes 120 is filter-type retention medium 130. The filter-type retention medium 130 can be a membrane filter (e.g., a polysulfone membrane filter) with a nominal porosity (e.g., 0.1 µm, 0.2 µm, 0.45 µm) suitable to retain the soluble or precipitable colored compound described herein.

In use, a liquid sample can be applied to one side of the filter-type retention medium 130 and the liquid can be allowed to pass through the retention medium by gravity force. Alternatively or additionally, the sample can be urged through the filter-type retention medium 130 by applying a positive-pressure source (not shown) to the through-hole 120 on the side of the filter-type retention medium 130 containing the sample or by applying a negative-pressure source (not shown) to the through hole 120 on the side of the filter-type retention medium 130 opposite the side containing the sample.

Figure 1B:
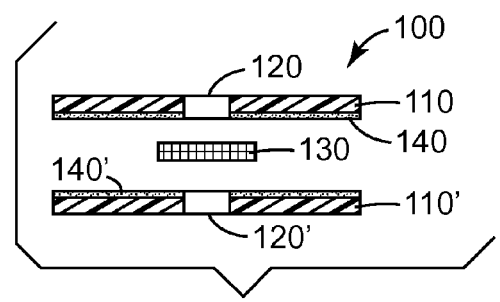
FIG. 1B is an exploded side view of the device of FIG. 1A.

FIG. 1B shows an exploded cross-sectional side view of the device 100 of FIG. 1A. The device 100 comprises an upper layer 110 and a lower layer 110', each comprising through-holes 120 and 120', respectively. The lower layer 110' can be constructed from materials as described for the upper layer 110. The upper layer 110 may be constructed from the same material as the lower layer 110'. In some embodiments, the upper layer 110 may be constructed from a different material as the lower layer 110'. Through-holes 120 and 120' are aligned to provide a liquid flow path starting at the upper surface and exiting the lower surface of the device 100. The adhesive 140 provides a water-resistant barrier surrounding the filter-type retention medium 130 that is aligned with the through-holes 120 and 120'. In some embodiments (not shown), the individual flow paths comprising the through-holes can be compartmentalized, such as in a 96-well plate format, for example.

Figure 2A:
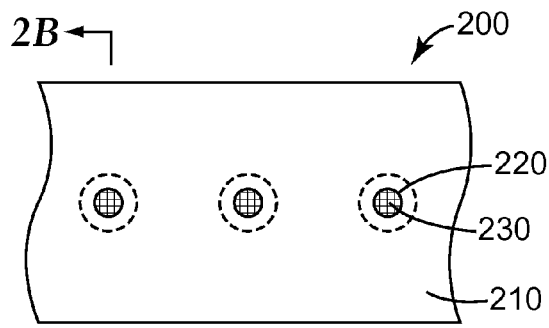
FIG. 2A is a top view of one embodiment of a device for detecting a nitrate compound or a nitrite compound according to the present disclosure.

FIG. 2A shows a top view of one embodiment of a device 200 for detecting NO$_x$ compounds in a sample. The device comprises an upper layer 210 with a plurality of through-holes 220. The upper layer 210 is preferably constructed from a water-resistant material (e.g., plastic, metal, glass, coated paper). In some embodiments, the upper layer 210 is constructed from a plastic film (e.g., a vinyl tape). In some embodiments, the upper layer 210 may be formed (e.g., by injection molding) with through-holes 220. In some embodiments, the through-holes 220 can be formed (e.g., via a hole punch or perforator) after the upper layer 210 is formed. Positioned beneath the upper layer 210 and coextensive with the cross-sectional area of the through-holes 220 is filter-type retention medium 230. The filter-type retention medium 230 can be a membrane filter (e.g., a polysulfone membrane filter) with a nominal porosity (e.g., 0.1 µm, 0.2 µm, 0.45 µm) suitable to retain the soluble or precipitable colored compound described herein.

Figure 2B:
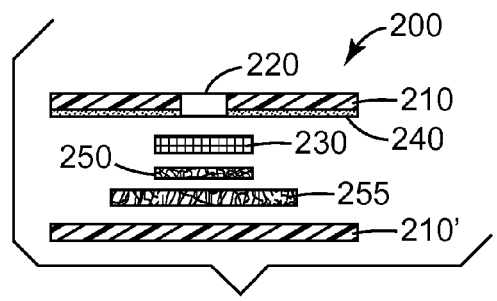
FIG. 2B is an exploded side view of the device of FIG. 3A.

FIG. 2B shows an exploded cross-sectional side view of the device 200 of FIG. 2A. The device 200 comprises an upper layer 210 comprising a through-hole 220. The lower layer 210' can be constructed without the through-hole from materials as described for the upper layer 210. In some embodiments, the upper layer 210 may be constructed from a different material as the lower layer 210'. Positioned adjacent the filter-type retention medium 230 on the side of the filter-type retention medium 230 opposite the through-hole 220 is an optional absorbent contact layer 250. Adjacent the contact layer 250, on the side of the contact layer 250 opposite the filter-type retention medium 230 is the absorbent reservoir 255. Both the contact layer 250 and absorbent reservoir 255 provide a wick to draw the liquid sample (not shown) through the filter-type retention medium 230. Contact layer 250 and absorbent reservoir 255 can be constructed from absorbent materials (e.g., cellulosic fibers, nonwovens, foams) and may be constructed from the same or different materials. Contact layer 250, if present, enhances the flow of liquid from filter-type retention medium 230 to the absorbent reservoir 255. The adhesive 240 couples the upper layer 210 to the lower layer 210', which facilitates contact between the absorbent reservoir 255 or the contact layer 250, if present, and the filter-type retention medium 230 and the adhesive 240 may provide a water-resistant barrier surrounding the filter-type retention medium 230 and the absorbent reservoir 255.

Nonlimiting examples of suitable materials for the contact layer 250 and/or absorbent reservoir 255 include Non-woven adsorbent (3M FAD absorbent pad), blotting paper (VWR Scientific), GF-B and TCLP (Whatman Corp.), Sterlitech glass fiber membranes (Sterlitech Corp.) with nominal pore sizes of 0.3 to 1.0 µm.

In any of the above embodiments, the method further can comprise using at least one reference mixture (e.g., one or more "standards") comprising a predetermined amount of a $NO_x$ compound (e.g., a nitrate salt). In some embodiments, the standard can comprise a threshold standard (e.g., for presence/absence tests). In some embodiments, a plurality of standards can be used to generate a standard curve for quantitative detection. In any of the above embodiments, detecting $NO_x$ in a sample further can comprise comparing the amount of $NO_x$ detected in the sample to the amount of $NO_x$ detected in one or more mixtures comprising a predetermined amount of $NO_x$ compound. In some embodiments, detecting $NO_x$ in a sample further can comprise comparing the amount of $NO_x$ detected in the sample to a standard curve.

In some embodiments, the colored compound (e.g., a red cationic dye) retained by the filter can be observed visually. In some embodiments, the soluble or precipitable colored compound retained by the filter can be detected or quantitated using an instrument (e.g., a reflection densitometer RD917, available from GretagMacbeth, Munich, Del.). The reflection densitometer can be used with any suitable filter to detect a red-colored compound. In some embodiments, a green filter can be used to detect a red-colored compound. In any of the above embodiments, the colored compound (e.g., a red cationic dye) can be detected and/or quantitated in a liquid solution or liquid suspension.

Kits:

The present disclosure provides kits for detecting $NO_x$ compounds in a sample. Kits may contain certain components that are packaged together for use in methods according to the present disclosure.

In one embodiment, the kit may comprise a retention medium (e.g., a filter-type retention medium, a particulate retention medium) and a chromogenic reagent that reacts with a nitrite compound to form a colored compound. The chromogenic reagent may comprise a chromogen and/or a developing agent. The kit may further comprise an agent to reduce a nitrate compound to a nitrite compound. In some embodiments, the kit may further comprise an acid (e.g., HCl).

In one embodiment, the kit may comprise a filter-type retention medium (or other retention media) and a compound selected from the group consisting of 4,4'-sulfonyldianiline, N-(1-naphthyl)ethylene-diamine, and $VCl_3$. In one embodiment, the kit may comprise a filter-type retention medium (or other retention media) and two or more compounds selected from the group consisting of 4,4'-sulfonyldianiline, N-(1-naphthyl)ethylene-diamine, and $VCl_3$. In any of the above embodiments, the kit may further comprise a strong acid. In some embodiments, the strong acid comprises HCl.

In any of the above embodiments, the kit further may comprise a sample acquisition device. In some embodiments, the sample acquisition device is adapted for obtaining a sample from a wound. In any of the above embodiments, the kit further may comprise a filtration device. In some embodiments, the filtration device can comprise the filter-type retention medium (or other retention media). In some embodiments, the filtration device can further comprise a mixing chamber in fluid communication with the filter-type retention medium. In some embodiments, the mixing chamber can be in selective fluid communication with the filter-type retention medium.

EXAMPLES

Objects and advantages of this invention are further illustrated by the following examples, but the particular materials and amounts thereof recited in these examples, as well as other conditions and details, should not be construed to unduly limit this invention.

All parts, percentages, ratios, etc. in the examples are by weight, unless noted otherwise. Solvents and other reagents used were obtained from Sigma-Aldrich Chemical Company (St. Louis, Mo.), unless otherwise noted.

Example 1

A set of nitrate standards were prepared from a stock solution of a potassium nitrate salt in water. The stock solution was further diluted in water to the following concentrations: 0, 5, 10, 15, 20, 25 and 30 µM, respectively. The diluted solutions were the "samples" used in the assay described below.

Reagent 1 was prepared by mixing 0.1 g of each of Components A and B with 49.8 g water. Component A consisted of a 1% (w/v) solution of dapsone (4,4'-sulfonyldianiline, Aldrich catalog no. A7480-7, Sigma-Aldrich, St. Louis, Mo.) in 1N HCl. Component B consisted of 0.05% (w/v) NEDD (N-(1-naphthyl)ethylene-diamine dihydrochloride, Eastman catalog no. 4835, Eastman Chemical Company, Kingsport, Tenn.) in water. Reagent 2 consisted of vanadium chloride ($VCl_3$) 0.1% (w/v) in 20% HCl.

Ten microliters of each sample was added to a microcentrifuge tube, where it was combined and mixed with 140 µl Reagent 1 and 20 µl Reagent 2. The tube was incubated at 70° C. for 10 min and cooled to room temperature. 830 µl of deionized water was added to the tube and the resulting mixture was filtered as described below.

Strips of white tape were perforated with 2.0 mm diameter holes. A laminate was formed by inserting membrane filter disks (¼ inch (6.35 mm) diameter, die-cut from Pall Gelman Lab I.C.E. 450, polysulfone membrane 0.45 µm, part number 66530) between two layers of tape such that the holes in the top layer of tape were superimposed over the holes in the bottom layer of tape with the filter membrane material located in the opening created by the superimposed holes. The laminate was placed over a 96-well plate configured for vacuum filtration such that a sample placed into the well of the plate could be drawn through the filter in the 2 mm opening. The membrane filter retained a red cationic dye in the samples containing a nitrite compound.

Figure 3:
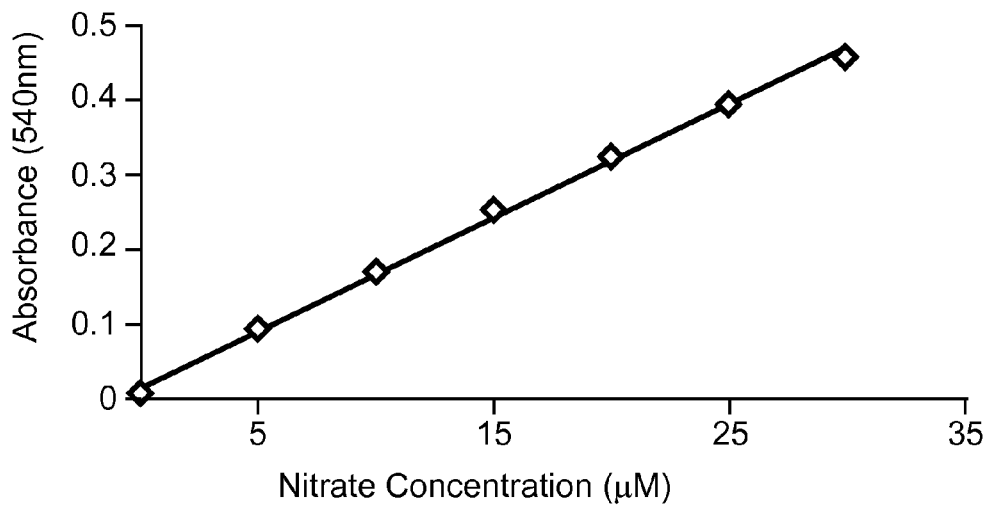
FIG. 3 is a graph of data from a reflective densitometer.

The intensity (optical density) of the color in each well was measured with a reflection densitometer (MacBeth RD917) using the green filter. A plot of the relationship between the concentration of nitrate compounds in the sample and the optical density of the color retained by the filter is shown in FIG. 3. The linearity of the reaction can be observed in this standard curve shown in FIG. 3.

Example 2

The detection system described in Example 2 was used to test the nitrate compound levels of various commercially-available absorbent materials. The materials included several grades of filter paper that are purported to contain extremely low levels of nitrates.

A standard containing 10 µM was prepared and tested as described in Example 1. Samples of absorbent materials (1 cm×1 cm squares of four grades of filter paper and one 3M NEXCARE Soft 'n Flex #672-35 first aid dressing) were placed in a tube and was wetted with 0.05 mL of the nitrate-free assay buffer (CaymanNitrate/Nitrite fluorometric assay kit, catalog no. 780051, Cayman Chemical Company) and was allowed to stand at room temperature for about 30 minutes. The buffer was extracted from the absorbent article by centrifugation at 10,000 rpm in a microcentrifuge, and 10 microliters of the extracted buffer was tested according to the procedure described in Example 1. The color of the membrane filters from the nitrate test from each absorbent material was compared to the color of the membrane filter of the 10 mM nitrate standard. Any test showing a darker shade of red than the standard was recorded as "yes". The results are shown in Table 1. The data indicate that all of the filter papers that were tested contained endogenous levels of nitrate compounds that are high enough to interfere with the detection of physiological levels of $NO_x$ using the method described in Example 1. In contrast, the first aid dressing did not contain endogenous levels of nitrate compounds that are high enough to interfere with the detection of physiological levels of $NO_x$ using the method described in Example 1.

TABLE 1

| Absorbent Article | Type | ≥10 μM |
|---|---|---|
| Filter | WHATMAN #5 | Yes |
| Filter | WHATMAN #40 | Yes |
| Filter | WHATMAN #50 | Yes |
| Filter | WHATMAN #54 | Yes |
| First Aid Dressing | 3M NEXCARE #672-35 | No |

Example 3

A set of nitrate standards were prepared from a stock solution of a potassium nitrate salt in water. The stock solution was further diluted in water to the following concentrations: 0, 5, 10, 15, 20, 25 and 30 μM, respectively. The diluted solutions were the "samples" used in the assay described below.

Reagent 1 was prepared by mixing 0.1 g of each of Components A and B with 49.8 g water. Component A consisted of a 1% (w/v) solution of dapsone (4,4'-sulfonyldianiline, Aldrich catalog no. A7480-7, Sigma-Aldrich, St. Louis, Mo.) in 1N HCl. Component B consisted of 0.05% (w/v) NEDD (N-(1-naphthyl)ethylene-diamine dihydrochloride, Eastman catalog no. 4835, Eastman Chemical Company, Kingsport, Tenn.) in water.

Reagent 2 consisted of vanadium chloride ($VCl_3$) 0.1% (w/v) in 20% HCl.

Ten microliters of each sample was added to a microcentrifuge tube, where it was combined and mixed with 140 μl Reagent 1 and 20 μl Reagent 2. The tube was incubated at 70° C. for 10 min and cooled to room temperature. 830 μl of deionized water was added to the tube and the resulting mixture was filtered as described below.

Strips of white tape were perforated with 2.0 mm diameter holes. A laminate was formed by inserting membrane filter disks (¼ inch (6.35 mm) diameter, die-cut from Pall Gelman Lab I.C.E. 450, polysulfone membrane 0.45 μm, part number 66530) between two layers of tape such that the holes in the top layer of tape were superimposed over the holes in the bottom layer of tape with the filter membrane material located in the opening created by the superimposed holes. The laminate was placed over a 96-well plate configured for vacuum filtration such that a sample placed into the well of the plate could be drawn through the filter in the 2 mm opening. The membrane filter retained the red cationic dye in the samples containing nitrate.

Figure 4:
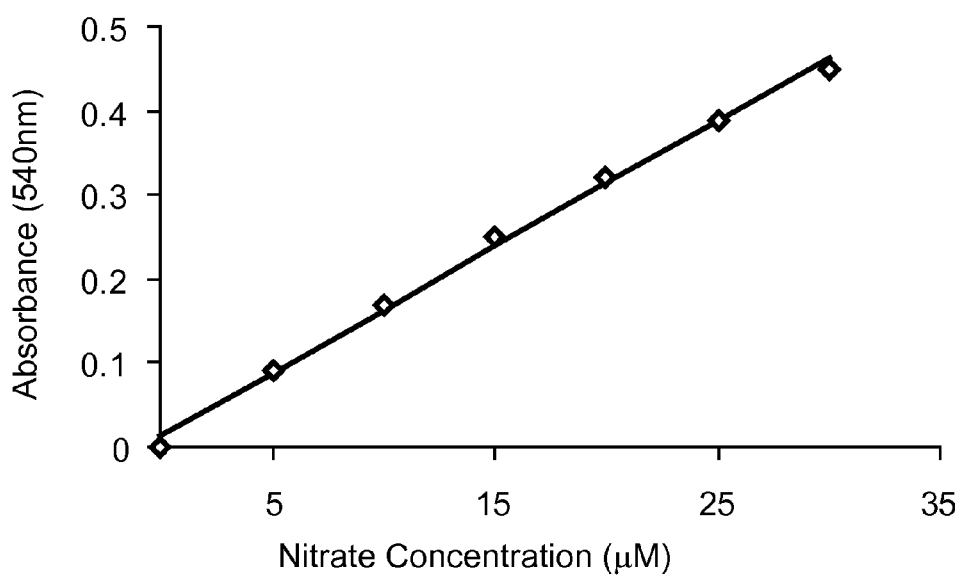
FIG. 4 is a graph of data from a spectrophotometer.

The intensity (optical density) of the color in each well was measured with a reflection densitometer (MacBeth RD917) using a green filter. A plot of the relationship between the concentration of nitrate in the sample and the optical density (O.D.) of the color retained by the filter is shown in FIG. 4.

Example 4

Figure 5:
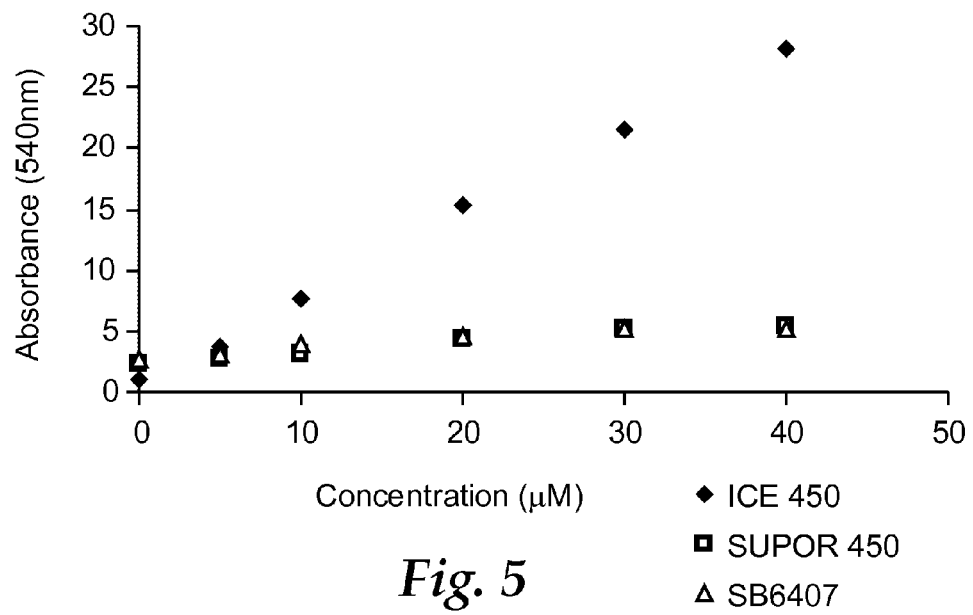
FIG. 5 is a graph of data from a reflective densitometer.

Calibration solutions of nitrate were prepared from potassium nitrate and DI water at 0, 5, 10, 20, 30 and 40 μM nitrate. A mixed reagent containing 0.05% w/v Vanadium (III) chloride, 0.25% w/v Dapsone, and 0.05% w/v Tsuda's reagent (N-(2-diethylaminoethyl)-1-naphthylamine oxalate, TCI Chemicals) was prepared in 10% HCl and filtered. Ten microliters of each calibration solution was reacted with 10 μL of the mixed reagent (diluted to 200 μL in DI water) and incubated at 70° C. for 10 min then cooled to room temperature. 300 μl of deionized water was added, and the resulting solution was filtered through 2 mm diameter membrane filters as described in Example 3. Three sets of membrane filters were used: 450 nm pore diameter uncharged (neutral) polysulfone membranes (Supor 450, Pall), 450 nm pore diameter anion-exchange polysulfone membranes (SB6407, Pall), and 450 nm pore diameter cation-exchange polysulfone membranes (I.C.E. 450, Pall). The reflectance of the adsorbed dye was measured using an X-Rite 530 (X-Rite Inc.) spectrodensitometer and the spectral scans converted to equivalent absorbance curves. The results, shown in Table 2 and FIG. 5, indicate that the cation-exchange membrane (I.C.E 450) was more efficient at capturing and retaining the cationic dye than the anion-exchange membrane (SB6407) or the uncharged membrane (SUPOR 450).

TABLE 2

Capture and retention of cationic dye on various membrane filters.

| | Absorbance of dye adsorbed on | | |
|---|---|---|---|
| Concentration of nitrate (μM) | Anion-exchange polysulfone membrane filter | Neutral polysulfone membrane filter | Cation-exchange polysulfone membrane filter |
| 0 | 2.75 | 2.19 | 1.06 |
| 5 | 3.11 | 2.63 | 3.75 |
| 10 | 4 | 3.18 | 7.62 |
| 20 | 4.47 | 4.35 | 15.31 |
| 30 | 5.08 | 5.21 | 21.61 |
| 40 | 5.07 | 5.48 | 28.08 |

Example 5

Calibration solutions of nitrate were prepared from potassium nitrate and DI water at 0, 5, 10, 20, 30 and 40 μM nitrate. A mixed reagent containing 0.05% w/v Vanadium (III) chloride, 0.25% w/v Dapsone, and 0.05% w/v Tsuda's reagent (N-(2-diethylaminoethyl)-1-naphthylamine oxalate, TCI Chemicals) was prepared in 10% HCl and filtered. The procedures for the spectrophotometric and colligative detection techniques were as follows.

Spectrophotometric Method:

40 μL of each of the calibration solutions was reacted with 80 μL of the mixed reagent and incubated at 70° C. for 10 min, then cooled to room temperature. 100 μl of each of the resulting dye solutions were transferred to a 96 well PS plate (Nunc) and read at 545 nm using a BioTek Synergy 4 plate reader.

Reflectance (Colligative) Method:

7 μL of each calibration solution was reacted with 14 μL of the mixed reagent (diluted to 200 μL in DI water) and incubated at 70° C. for 10 min, then cooled to room temperature. 300 μl of deionized water was added, and the resulting solutions were filtered through 2 mm diameter membrane filters as described in Example 3.

Figure 6:
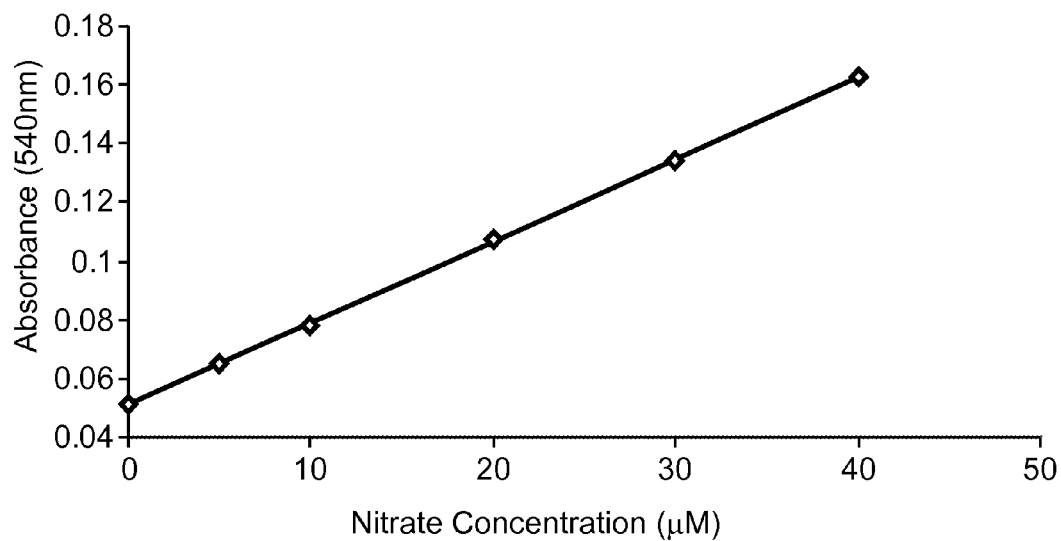
FIG. 6 is a graph of data from a spectrophotometer.
Figure 7:
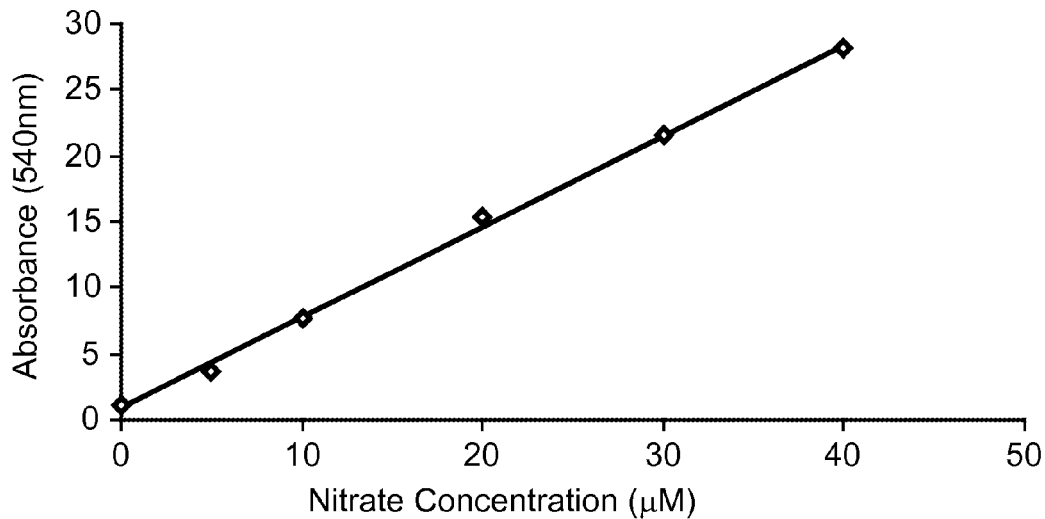
FIG. 7 is a graph of data from a reflective densitometer.

The results, shown in FIGS. 6 and 7, demonstrate the higher sensitivity of the colligative technique which requires less sample volume than used for the spectrophotometric method. Both assays showed a linear response to the concentration of nitrate. The correlation coefficient ($R^2$) for the spectrophotometric method was 0.9999. The correlation coefficient for the reflectance method was 0.9983. In addition, the discriminatory power of the assay, as measured by the slope of the calibration line, is over 200 times higher for the colligative method.

Example 6

This example demonstrates the insensitivity of the colligative detection system to biological matrices when compared with a conventional spectrophotometric detection assay for nitrate, allowing for biological sample processing without clean-up.

Calibration solutions of nitrate were prepared from potassium nitrate and DI water at 0, 5, 10, 20, 30 and 40 μM nitrate in 10% reconstituted human plasma (Sigma Chemicals). A mixed reagent containing 0.05% w/v Vanadium (III) chloride, 0.25% w/v Dapsone, and 0.05% w/v Tsuda's reagent (N-(2-diethylaminoethyl)-1-naphthylamine oxalate, TCI Chemicals) was prepared in 10% HCl and filtered. The procedures for the spectrophotometric and colligative detection techniques were as follows:

Spectrophotometric Method:

40 μL of each of the calibration solutions was reacted with 80 μL of the mixed reagent and incubated at 70° C. for 10 min, then cooled to room temperature. 100 μl of each of the resulting dye solutions were transferred to a 96 well PS plate (Nunc) and read at 545 nm using a BioTek Synergy 4 plate reader.

Colligative Method:

7 μL of each calibration solution was reacted with 14 μL of the mixed reagent (diluted to 200 μL in DI water) and incubated at 70° C. for 10 min, then cooled to room temperature. 300 μl of deionized water was added, and the resulting solutions were filtered through 2 mm diameter membrane filters as described in Example 3.

Figure 8:
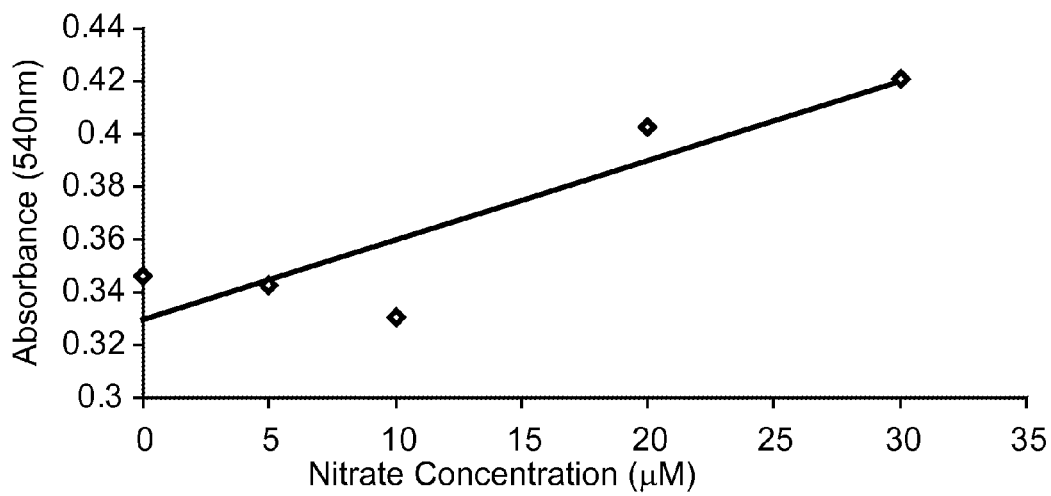
FIG. 8 is a graph of data from a spectrophotometer.
Figure 9:
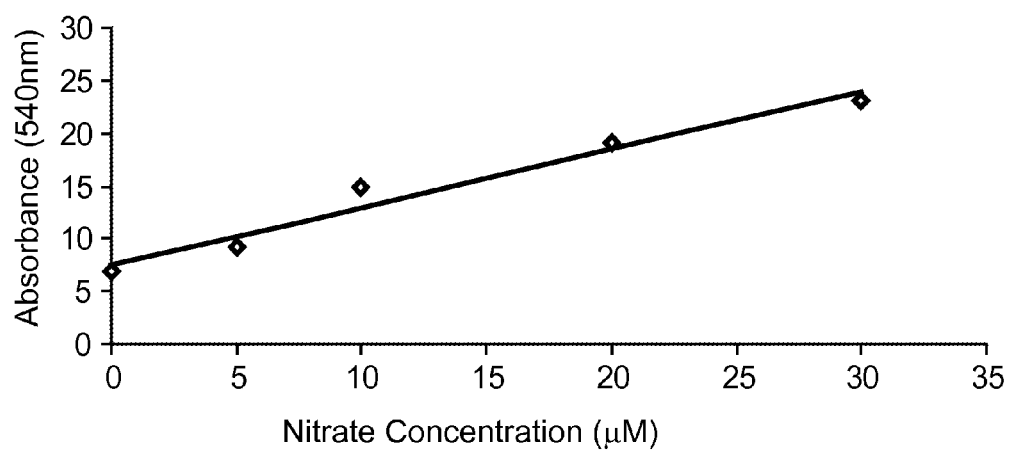
FIG. 9 is a graph of data from a reflective densitometer.

The results shown in FIGS. 8 and 9 indicate the scattering influence of plasma protein in acidic media on the absorbance measurements in the spectrophotometric method. The scattering leads to non-linearity in the calibration curve for the spectrophotometric method (correlation coefficient=0.7982). The colligative method produces a linear relationship between nitrate concentration and absorbance (correlation coefficient=0.9644).

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

The invention claimed is:

1. A method of detecting a $NO_x$ compound in a wound, comprising:
   providing a sample from a wound, a first retention medium, and a chromogenic reagent;
      wherein the chromogenic reagent is capable of reacting with a nitrite compound to form a colored compound;
      wherein the first retention medium is configured to retain the colored compound
   forming a first mixture comprising the sample and the chromogenic reagent under conditions that permit the reaction of a nitrite compound with the chromogenic reagent to form the colored compound;
   heating the first mixture;
   diluting the first mixture with an aqueous liquid;
   contacting at least a portion of the first mixture with the first retention medium; and
   detecting the colored compound retained on the first retention medium;
   wherein the first retention medium comprises a medium with ionic functional groups that interact with the colored compound;
   wherein the contacting at least a portion of the first mixture with the first retention medium occurs after the heating the first mixture and after the diluting the first mixture with an aqueous liquid.

2. The method of claim 1, further comprising providing a reducing agent, wherein the first mixture includes the reducing agent, wherein the conditions simultaneously permit the reduction of nitrate compound to a nitrite compound and permit the reaction of a nitrite compound with the chromogenic reagent to form the colored compound.

3. The method of claim 1, wherein the chromogenic reagent comprises a chromogen or a developing agent.

4. The method of claim 1, wherein the chromogenic reagent is selected from the group consisting of, 4,4'-Bis-(dimethylamino)thiobenzophenone; azulene; brucine indol; p-phenylazoaniline; p-nitroaniline; anthranilic acid; p-aminoacetophenone; p-aminophenylsulphone; p-phenylaniline; sulphanilic acid; bis-(4-aminophenyl)sulphide; (4-aminophenyl)trimethylammonium chloride; 1-naphthylamine; chloro-p-phenylenediamine; resorcinol; N,N-dimethylaniline; 4 nitro-1-naphthylamine; p-phenylazoaniline; 4 nitro-1-naphthylamine; p-aminoacetophenone; 1 anilinonaphthylene; 1-naphthol; benzaldehyde 2-benzothiazolylhydrazone; anthrone; 1-anthrol; diphenylamine; 1,2-dihydroxybenzene; sesamol; N,N-dimethyl-1-naphthylamine; formaldehyde; iron(III) perchlorate; and N,N-dimethyl-3-hydroxyaniline.

5. The method of claim 1, wherein detecting a colored compound comprises detecting the colored compound visually.

6. The method of claim 1, wherein detecting a colored compound comprises detecting the colored compound quantitatively.

7. The method of claim 1, further comprising:
   forming a second mixture comprising a predetermined amount of a $NO_x$ compound and a chromogenic reagent that reacts with a nitrite compound to form a colored compound;
   contacting at least a portion of the second mixture with a second retention medium configured to retain the colored compound;
   detecting the colored compound retained on the second retention medium; and
   comparing the amount of colored compound retained on the first retention medium with the amount of colored compound retained on the second retention medium.

8. The method of claim 7, wherein the first or second retention medium comprises a medium with ionic functional groups.

9. The method of claim 1, wherein contacting at least a portion of the mixture with a retention medium comprises contacting the portion with a membrane filter.

10. The method of claim 9, wherein contacting the portion with a membrane filter comprises contacting the portion with a membrane filter having a contact surface area of about 1.5 mm$^2$ to about 31 mm$^2$.

11. The method of claim 1, wherein detecting the colored compound comprises detecting the colored compound using an instrument.

* * * * *

UNITED STATES PATENT AND TRADEMARK OFFICE
CERTIFICATE OF CORRECTION

| | | |
|---|---|---|
| PATENT NO. | : 8,617,897 B2 | Page 1 of 1 |
| APPLICATION NO. | : 13/388564 | |
| DATED | : December 31, 2013 | |
| INVENTOR(S) | : Vinod P. Menon | |

It is certified that error appears in the above-identified patent and that said Letters Patent is hereby corrected as shown below:

In the Specification

<u>Column 3,</u>
Line 29, "N,N-dimethyl-3-hydroxy aniline." should read --N,N-dimethyl-3-hydroxyaniline.--.

In the Claims

<u>Column 18,</u>
Line 43, "4 nitro-1-naphthylamine;" should read --4-nitro-1-naphhylamine;--.
Lines 43-44, "4 nitro-1-naphthylamine;" should read --4-nitro-1-naphhylamine;--.
Lines 44-45, "1 anilinonaphthylene;" should read --1-anilinonaphthylene;--.

Signed and Sealed this
Fifth Day of May, 2015

Michelle K. Lee
*Director of the United States Patent and Trademark Office*